US010779386B2

(12) United States Patent
Limmer et al.

(10) Patent No.: US 10,779,386 B2
(45) Date of Patent: Sep. 15, 2020

(54) GUIDE DEVICE AND X-RAY DEVICE

(71) Applicant: SIEMENS HEALTHCARE GMBH, Erlangen (DE)

(72) Inventors: Andreas Limmer, Fuerth (DE); Zsolt Pavel, Bubenreuth (DE); Norbert Scherer, Nuremberg (DE); Friedrich Schirmer, Buch am Wald (DE)

(73) Assignee: Siemens Healthcare GmbH, Erlangen (DE)

( * ) Notice: Subject to any disclaimer, the term of this patent is extended or adjusted under 35 U.S.C. 154(b) by 714 days.

(21) Appl. No.: 15/467,135

(22) Filed: Mar. 23, 2017

(65) Prior Publication Data

US 2017/0280541 A1    Sep. 28, 2017

(30) Foreign Application Priority Data

Mar. 23, 2016 (DE) .................. 10 2016 204 832

(51) Int. Cl.
| | |
|---|---|
| *H05G 1/02* | (2006.01) |
| *H02G 11/02* | (2006.01) |
| *B65H 75/44* | (2006.01) |
| *A61B 6/00* | (2006.01) |

(52) U.S. Cl.
CPC ............. *H05G 1/02* (2013.01); *A61B 6/4441* (2013.01); *B65H 75/4449* (2013.01); *H02G 11/02* (2013.01); *B65H 2701/34* (2013.01)

(58) Field of Classification Search
CPC .............. A61B 6/4441; B65H 2701/34; B65H 75/4449; H02G 11/02; H05G 1/02
See application file for complete search history.

(56) References Cited

U.S. PATENT DOCUMENTS

| | | | | |
|---|---|---|---|---|
| 4,063,097 A | * | 12/1977 | Barrett ................... | A61B 6/032 378/18 |
| 4,065,066 A | * | 12/1977 | Swett ....................... | A61B 6/56 242/364.9 |
| 4,065,978 A | * | 1/1978 | Meresz .................... | A61B 6/56 74/82 |
| 4,443,888 A | * | 4/1984 | Cutter .................... | G01B 7/026 33/713 |
| 4,565,333 A | * | 1/1986 | Meneian ................. | H02G 11/02 242/365.2 |
| 4,802,197 A | * | 1/1989 | Juergens .............. | A61B 6/4441 378/194 |

(Continued)

FOREIGN PATENT DOCUMENTS

DE            19651960 C1      3/1998

*Primary Examiner* — David J Makiya
*Assistant Examiner* — Soorena Kefayati
(74) *Attorney, Agent, or Firm* — Laurence Greenberg; Werner Stemer; Ralph Locher (57) ABSTRACT

A guide device for at least one line, such as an electric line of a C-arm, has a rotatable first cylinder with a first cylindrical surface and a static second cylinder, adjoining the first cylinder in the axial direction and having a second cylindrical surface. A first guide element for guiding the line on the first and/or the second cylindrical surface, is disposed coaxially with respect to the first and the second cylinder and it is movable relative to the first and the second cylinder. The line can be wound up on the first and/or the second cylindrical surface or can be unwound therefrom depending on the movement of the first cylinder.

16 Claims, 6 Drawing Sheets

(56) References Cited

U.S. PATENT DOCUMENTS

| | | | | |
|---|---|---|---|---|
| 5,145,390 A * | 9/1992 | Kaul | A61B 6/56 | 242/388.6 |
| 5,450,466 A * | 9/1995 | Kadowaki | A61B 6/4405 | 378/189 |
| 5,863,010 A * | 1/1999 | Boomgaarden | A61B 6/4405 | 242/388 |
| 5,899,401 A * | 5/1999 | Reimann | A61B 6/447 | 242/372 |
| 5,980,107 A * | 11/1999 | Kusch | H02G 11/02 | 378/194 |
| 6,065,710 A * | 5/2000 | Richter | A61B 6/56 | 191/12.2 R |
| 6,164,820 A * | 12/2000 | Hell | A61B 6/032 | 378/119 |
| 6,250,443 B1 * | 6/2001 | Richter | A61B 6/56 | 191/12.2 R |
| 6,361,237 B1 * | 3/2002 | Salmela | F16L 3/012 | 285/121.3 |
| 6,789,941 B1 * | 9/2004 | Grady | A61B 6/504 | 378/197 |
| 9,126,802 B2 * | 9/2015 | Holmberg | B65H 75/38 | |
| 2007/0280426 A1 * | 12/2007 | Saffer | A61B 6/4441 | 378/198 |
| 2009/0190721 A1 * | 7/2009 | Lv | F16M 11/18 | 378/167 |
| 2010/0121604 A1 * | 5/2010 | Vaisburd | G01C 9/00 | 702/154 |
| 2011/0024543 A1 * | 2/2011 | Smrha | B65H 75/4471 | 242/377 |
| 2012/0106701 A1 * | 5/2012 | Meek | H05G 1/02 | 378/62 |
| 2012/0121071 A1 * | 5/2012 | Herrmann | A61B 6/56 | 378/194 |
| 2013/0065413 A1 * | 3/2013 | Adachi | H02G 11/02 | 439/164 |
| 2013/0289542 A1 * | 10/2013 | Nyman | A61B 90/50 | 606/1 |
| 2014/0263796 A1 * | 9/2014 | Sparrowhawk | H02G 11/02 | 242/377 |
| 2015/0321876 A1 * | 11/2015 | Galindo Gonzalez | B65H 75/40 | 242/611 |
| 2018/0028136 A1 * | 2/2018 | Manetti | A61B 6/508 | |
| 2018/0310902 A1 * | 11/2018 | Rowland | A61B 6/105 | |

* cited by examiner

GUIDE DEVICE AND X-RAY DEVICE

CROSS-REFERENCE TO RELATED APPLICATION

This application claims the priority, under 35 U.S.C. § 119, of German patent application DE 10 2016 204 832.5, filed Mar. 23, 2016; the prior application is herewith incorporated by reference in its entirety.

BACKGROUND OF THE INVENTION

Field of the Invention

The invention relates to a guide device for at least one line, in particular an electric line of a C-arm. The guide device has a rotatable first cylinder with a first cylindrical surface. The line can be wound up onto the first cylindrical surface or can be unwound therefrom depending on the movement of the first cylinder.

Guide devices of this type are known from the prior art. In particular in the case of C-arms, the lines which lead to the radiation source and to the detector have to be wound up or unwound during a movement of the C-arm about its orbital axis, i.e., the axis about which the detector and the radiation source rotate during a movement of the C-arm, in accordance with the direction of movement. For this purpose, it is furthermore known that two guide devices are provided, wherein one guide device comprises the line for the detector and the second guide device comprises the line for the radiation source. During a movement of the C-arm about the orbital axis, the line of one of the two guide devices is consequently unwound and at the same time the other line, which is assigned to the other guide device, is wound up onto the latter.

It should be noted here that the two guide devices always have to be coupled in terms of movement to each other in such a manner that the winding-up operation of the one guide device corresponds to the unwinding operation of the other guide device. For this purpose, for example, a coupling of the two guide devices in terms of movement is necessary. In addition, it is necessary always to provide the two guide devices, but this may be disadvantageous in environments with limited space provision. Consequently, less space is available for the operator or the user of the C-arm, which is disadvantageous, for example, in the operating rooms or operation rooms in which the C-arm is used. In particular in respect of mobile C-arms, it is therefore desirable to make a more compact construction possible.

SUMMARY OF THE INVENTION

It is accordingly an object of the invention to provide a guide device and an x-ray device which overcomes the above-mentioned and other disadvantages of the heretofore-known devices and methods of this general type.

With the foregoing and other objects in view there is provided, in accordance with the invention, a guide device for at least one line, such as an electrical line of a C-arm. The novel guide device comprises:

a rotatable first cylinder having a first cylindrical surface;

a static second cylinder, adjoining said first cylinder in an axial direction and having a second cylindrical surface;

a first guide element configured for guiding the line on said first cylindrical surface and/or on said second cylindrical surface, said first guide element being arranged coaxially with respect to said first and second cylinders and being movable relative to said first and second cylinders; and wherein said rotatable cylinder, said static cylinder, and said first guide element are configured to enable the line to be wound up on said first cylindrical surface and/or said second cylindrical surface, or to be unwound therefrom, depending on a movement of said first cylinder.

In other words, the objects of the invention are achieved with a guide device of the type mentioned at the beginning with a static second cylinder, adjoining the first cylinder in the axial direction and having a second cylindrical surface, and a first guide element, guiding the line on the first and/or the second cylindrical surface, being arranged coaxially with respect to the first and the second cylinder and being movable relative to the first and the second cylinder, are provided, and in that the line can be wound up on the first and/or the second cylindrical surface or can be unwound therefrom depending on the movement of the first cylinder.

According to the invention, a first rotatable cylinder and a second static cylinder are consequently provided. The first cylinder is rotatable relative to the second cylinder. The second cylindrical surface which is assigned to the second cylinder is stationary relative to the first cylindrical surface which is assigned to the first rotatable cylinder. The rotation of the first cylinder runs here about the common cylinder axis. Since the two cylinders adjoin each other in the axial direction, they form a common cylindrical surface, wherein the first cylindrical surface is rotatable and the second cylindrical surface is static. A guide element is provided coaxially with respect to the first and the second cylinder, said guide element winding up the line on the first and/or the second cylindrical surface or unwinding said line therefrom depending on the movement of the first cylinder.

The guide element is movable relative to the first cylinder and the second cylinder and engages around the first and/or the second cylinder or the cylindrical surfaces thereof. The guide element is preferably movable here in a translatory manner in the axial direction and in a rotatory manner about the axis of rotation of the two cylinders. During such a rotatory and translatory movement, the guide element guides the line on the first and/or the second cylindrical surface and winds the line onto the latter or unwinds the line therefrom depending on the movement of the first cylinder. The guide element is substantially moved by the line itself which loops around the guide element or is guided thereon. In other words, the first cylinder, onto the first cylindrical surface of which the line is wound at least in sections, moves the line in a rotatory manner about the axis of rotation of the two cylinders. By means of this movement, the guide element is likewise moved in a rotatory manner about the axis of rotation, and therefore the line is guided by the guide element. By means of the rotatory movement about the axis of rotation, the line, guided by the guide element, is wound up on or unwound from the second cylindrical surface. The guide element is moved in a translatory manner along the axis of rotation of the two cylinders depending on the winding-up state or unwinding state. The movement along the axis of rotation of the guide element comes about by the fact that, during the winding-up operation, windings of the line are added on the second cylinder and the guide element is moved by said windings of the line in the axial direction toward the first cylinder. During the unwinding operation, windings of the line on the static cylinder are reduced, and therefore the guide element is moved in the axial direction towards the second cylinder. It is accordingly advantageously possible for the line to be wound up or unwound depending on the direction of rotation of the first cylinder.

It is particularly preferably provided in the case of the guide device according to the invention that at least one further rotatable third cylinder and at least one further static fourth cylinder and at least one further second guide element are provided, which are arranged about the axis of rotation of the guide device coaxially with respect to the first cylinder and the second cylinder, wherein at least one further line can be wound up on and can be unwound from the at least one further third cylindrical surface of the third cylinder and/or fourth cylindrical surface of the fourth cylinder.

According to this refinement of the guide device according to the invention, it is provided that the first and the second cylinder and the first guide element are arranged coaxially on the inside with respect to the third cylinder and the fourth cylinder and the second guide element. Consequently, a first assembly consisting of the first and the second cylinder and the first guide element, and a second assembly consisting of the third cylinder and the fourth cylinder and the second guide element are formed. The second assembly engages here around the first assembly. The axis of rotation of the guide device is both the axis of rotation of the first cylinder and also the axis of rotation of the third cylinder. The first cylinder is rotatable here relative to the second cylinder, and the third cylinder is rotatable relative to the fourth cylinder. The first assembly substantially corresponds to the basic construction according to the second assembly, and therefore a further second line can be wound up on the second assembly and can be unwound therefrom in the same manner as the first line can be wound up on and unwound from the first assembly.

As a result, it is possible for the first line to be wound up on or unwound from the common cylindrical surface, which is formed from the first cylindrical surface and the second cylindrical surface, during a movement of the first cylinder. Accordingly, the second line is wound up on or unwound from the common cylindrical surface, which is formed from the third cylindrical surface and the fourth cylindrical surface, during a movement of the third cylinder. Consequently, the first line and the second line run separately from each other on the first assembly and on the second assembly, and therefore unwinding of the first line and simultaneous winding up of the second line, or vice versa, is possible.

It can particularly preferably be provided here that a winding direction of the line and a winding direction of the at least one further line or of one of the further lines differ. As a result, it can particularly preferably be provided that the two rotatable cylinders, i.e. the first cylinder and the third cylinder, are coupled to each other in such a manner that, as the first line is wound up, the second line is unwound in a manner corresponding to the winding-up operation of the first line, and vice versa. As a result, the first line can be assigned, for example, to the detector and can run in or on the housing of the C-arm, and the second line can be assigned to the radiation source and can run in or on the housing of the C-arm. During the unwinding of the first line, the second line is wound up in the correct proportion, and vice versa, and therefore the required length of the line is always available and a movement of the C-arm is not obstructed.

As already described previously, the guide element or the guide elements is or are preferably rotatable about the axis of rotation of the guide device and/or movable in the axial direction along the cylindrical surface of the rotatable and/or the static cylinder to which said guide element or guide elements is or are assigned. It is ensured by means of the guide element or the guide elements that the line is efficiently wound on the corresponding cylindrical surface, and therefore the required construction space for the guide device can be optimally used. The guide element moves here in a manner force-coupled to the line which loops therearound and guides same in turn on the static cylindrical surface.

It is provided in a development of the guide device according to the invention that the at least one static cylinder has a deflection deflecting the line from an interior space of the static cylinder onto the static cylindrical surface. Accordingly, it is provided that the at least one line runs through the interior space of the static cylinder, for example the second cylinder, and is deflected onto the static cylindrical surface by means of the deflection. The deflection is preferably located here in the axial direction on an end region, in particular on that end of the static cylinder which faces away from the rotatable cylinder, and deflects the line there onto the static cylindrical surface, and therefore the line is wound on the static cylindrical surface from the end facing away from the rotatable cylinder in the direction of the rotatable cylinder.

In a further refinement of the guide device according to the invention, it can be provided that a casing element which surrounds the at least one static cylinder and the at least one rotatable cylinder and the at least one guide element at least in sections, is arranged coaxially and is coupled to the rotatable cylinder or to one of the rotatable cylinders is provided. The casing element engages around or surrounds the at least one rotatable cylinder and the at least one static cylinder and the at least one guide element. The casing element is arranged here coaxially with respect to the axis of rotation of the guide device.

It can be particularly preferably provided here that the casing element has at least one deflection deflecting the line from an interior of the casing element onto the casing surface of the casing element. Consequently, the at least one line is guided by the deflection onto the casing surface of the casing element. The line consequently runs from the interior space of the static cylinder over the static cylindrical surface and loops around the guide element, after which the latter runs over the cylindrical surface of the rotatable cylinder and is subsequently deflected by the deflection of the casing element onto the casing surface of the casing element.

In a particularly preferred refinement of the guide device according to the invention, the latter has two guide elements and two rotatable cylinders and two static cylinders, wherein the casing element surrounds or engages around the two guide elements and the two rotatable cylinders and the two static cylinders at least in sections, and the two lines are wound on the casing surface in an opposed winding direction depending on the winding-up state or the unwinding state. The casing element here has two deflections, wherein one deflection in each case is assigned to one of the two lines. Consequently, the first deflection directs the first line onto the casing surface and the second deflection directs the second line onto the casing surface in an opposed winding direction.

The casing surface is preferably coupled here to the first and/or the third cylinder in such a manner that, during a movement of the first and of the third cylinder, the casing surface is rotated at the same time about the axis of rotation of the guide device. Consequently, the first line is wound up on or unwound from the casing surface depending on the direction of rotation, and the second line is correspondingly unwound or wound up in an opposed manner to the first line. Starting from the completely wound-up state of the first line, the latter is first or all unwound from the casing surface during an unwinding operation in order subsequently to be moved on the first cylindrical surface by the movement of the first cylinder. The first line is unwound here from the first cylindrical surface at the end facing the deflection of the casing element and is wound up again onto the first cylindrical surface on the side of the end facing the second cylinder, i.e. the portion of the line which lies against the guide element on the side of the rotatable cylinder. The guide element moves here in a rotatory manner about the axis of rotation of the guide device and in a translatory manner in the direction of the free end of the second cylinder. The windings of the first line on the second cylindrical surface are unwound here and guided by the guide element onto the first cylindrical surface from where said line is guided by the deflection of the casing element. The operation proceeds precisely in reverse as the first line is being wound up. Similarly, the described winding-up operation can be transferred to the second line which is correspondingly wound up on the third cylindrical surface or the fourth cylindrical surface and is guided by the second guide element. Of course, if further static and/or rotatable cylinders are provided, the described operation can also be transferred thereto.

The at least one deflection of the casing element preferably has a groove-shaped or trench-shaped portion on the casing surface. The corresponding line is guided out of the deflection onto the casing surface by means of the groove-shaped or the trench-shaped portion. Secure guidance or deflection of the line onto the casing surface is ensured by the portion which is recessed by means of the groove or the trench.

A preferred refinement of the guide device furthermore makes provision for the at least one guide element to be of U-shaped or C-shaped design. The at least one guide element is therefore substantially designed as an open ring an engages around the static and/or the dynamic cylinder to which it is assigned. The opening in the ring shape or in the region of the opening in the ring shape, i.e. ultimately the free portion of the U-shaped or C-shaped guide element, serves for guiding the line. The latter loops around the guide element on both sides of the annular cross section and is deflected in the region of the opening, in particular from the rotatable cylindrical surface onto the static cylindrical surface.

It can be particularly preferably provided here that the winding directions of the line, which is assigned to the at least one guide element, in the region of the rotatable cylinder and in the region of the static cylinder differ, and/or in that the winding direction of the line is reversed on the deflecting portion. In the region of the opening, the guide element has the deflecting portion on which the line coming from the rotatable cylinder is deflected onto the static cylinder, or vice versa. The deflecting portion has a first deflecting side and a second deflecting side against which the line bears depending on the direction of rotation of the rotatable cylinder and therefore depending on whether the line is being wound up or unwound.

In a further refinement of the guide device according to the invention, it can be provided that said guide device can be coupled or is coupled to a drive device which is designed to move the at least one rotatable cylinder. By means of the drive device, the at least one rotatable cylinder is moved, depending on the direction of movement of the C-arm, and therefore the line assigned to said cylinder is unwound or wound up. It is possible here to use the drive device of the C-arm, which drive device is correspondingly coupled to the at least one rotatable cylinder, and therefore said cylinder can be actively moved in accordance with the movement of the C-arm. Alternatively, a drive device of the rotatable cylinder can be dispensed with, and therefore the latter, forcibly coupled by the fastening of the line to the C-arm, is moved by pull/or push forces acting on the line during a movement of the C-arm.

If a drive device is provided, the latter can be designed as a hub motor and can be arranged in the interior of the rotatable cylinder or of the radially innermost rotatable cylinder. The drive device is arranged here likewise coaxially with respect to the axis of rotation of the guide device and is arranged in the interior of the radially innermost rotatable cylinder. Similarly, the drive device can be designed as a belt drive which is coupled to the at least one rotatable cylinder.

A development of the guide device according to the invention can furthermore consist in that the at least one static cylinder has a fastening point for the line assigned thereto or can be connected or is connected to a fastening point for the line assigned thereto. The at least one line is therefore firstly fastened to the C-arm, in particular in the region of the device to which said line is assigned, for example the detector or the radiation source. In addition, the static cylinder, to which the at least one line is assigned, likewise has a fastening point or can be coupled or is coupled to such a fastening point.

In addition, the invention relates to a C-arm X-ray device, in particular a mobile C-arm, which comprises a guide device according to the invention. It is particularly preferably provided in the case of the X-ray device according to the invention that a movement of the at least one rotatable cylinder is coupled to a movement of the X-ray device, in particular a movement of the detector and of the X-ray emitter about the orbital axis. Of course, all of the details and features of the guide device according to the invention can be transferred to the X-ray device according to the invention.

Other features which are considered as characteristic for the invention are set forth in the appended claims.

Although the invention is illustrated and described herein as embodied in a guide device and x ray device, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Figure 1:
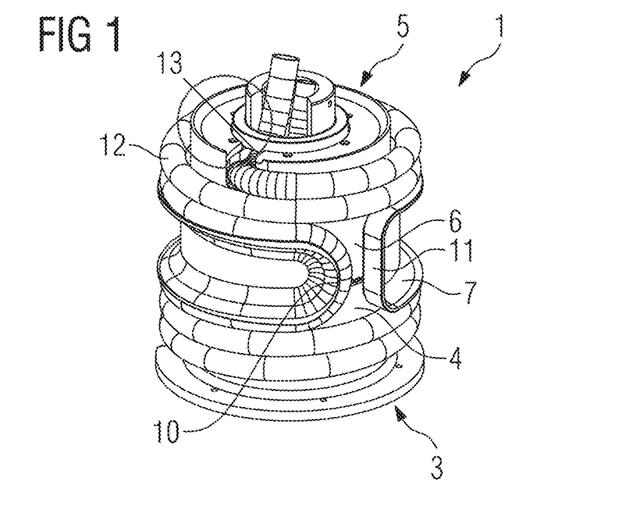
FIG. 1 is a perspective view of a first assembly of a guide device according to the invention.
Figure 2:
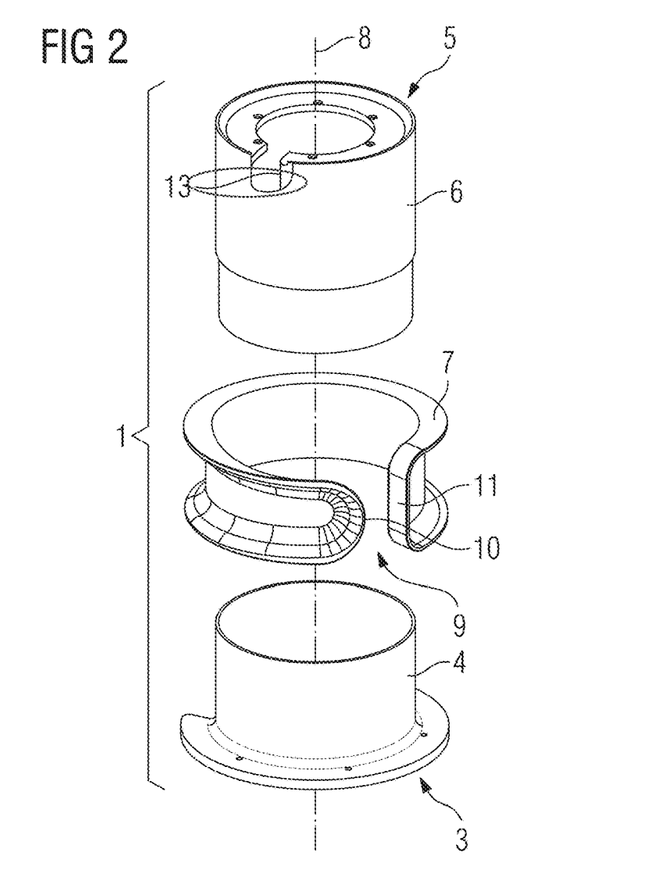
FIG. 2 shows an exploded illustration of the first assembly from FIG. 1.

Referring now to the figures of the drawing in detail and first, particularly, to FIG. 1 thereof, there is shown a first assembly 1 of a guide device 2 in a perspective illustration. The principle according to the invention will be illustrated below using the first assembly 1 with reference to FIGS. 1 to 4. The manner of operation of the entire guide device 2 will then be discussed.

The first assembly 1 of the guide device 2 has (cf. FIGS. 1 and 2) a first rotatable cylinder 3 with a first cylindrical surface 4, a second static cylinder 5 with a second cylindrical surface 6, and a first guide element 7. As can be seen, the first cylinder 3, the second cylinder 5 and the first guide element 7 are arranged coaxially about an axis of rotation 8 of the guide device 2. In the assembled state which is shown in FIG. 1, the first cylindrical surface 4 and the second cylindrical surface 6 adjoin each other; they preferably have the same radius. The first cylinder 3 is arranged here rotatably relative to the second cylinder 5. The first guide element 7 engages around the first cylindrical surface 4 and the second cylindrical surface 6 and is arranged rotatably both in a translatory manner along the axis of rotation 8 and in a rotatory manner about the axis of rotation 8. As can be seen, the first guide element 7 is of substantially C-shaped construction and therefore substantially has an open ring shape. In the region of the opening of the first guide element 7, the latter has a deflecting portion 9 which has a first deflecting side 10 and a second deflecting side 11. Consequently, the first assembly 1 comprises the first cylinder 3, the second cylinder 5 and the first guide element 7.

As is furthermore apparent in FIG. 1, the first assembly 1 is assigned a first line 12 which, in FIG. 1, is partially wound up onto the first cylindrical surface 4 and the second cylindrical surface 6. As can be seen, FIG. 1 shows a state which lies between the unwinding state and the winding-up state and will also be discussed below. It can furthermore be seen in FIG. 1 that the first line 12 is wound up in in each case approx. two windings on the first cylindrical surface 4 and the second cylindrical surface 6 and loops around the first guide element 7. The first line 12 lies here against the first deflecting side 10 of the first guide element 7. In the region of the free end of the second cylinder 5, the second cylinder 5 has a first deflection or deflection wall 13 by means of which the first line 12 is guided into the interior of the second cylinder 5 or is guided out of the interior of the second cylinder 5 onto the second cylindrical surface 6. Furthermore, it can be seen from FIG. 1 that the winding direction of the first line 12 changes in the region of the deflection 9 of the first guide element 7. Consequently, the first line 12 is wound on the first cylindrical surface 4 in a manner opposed to the winding direction on the second cylindrical surface 6.

Figure 3:
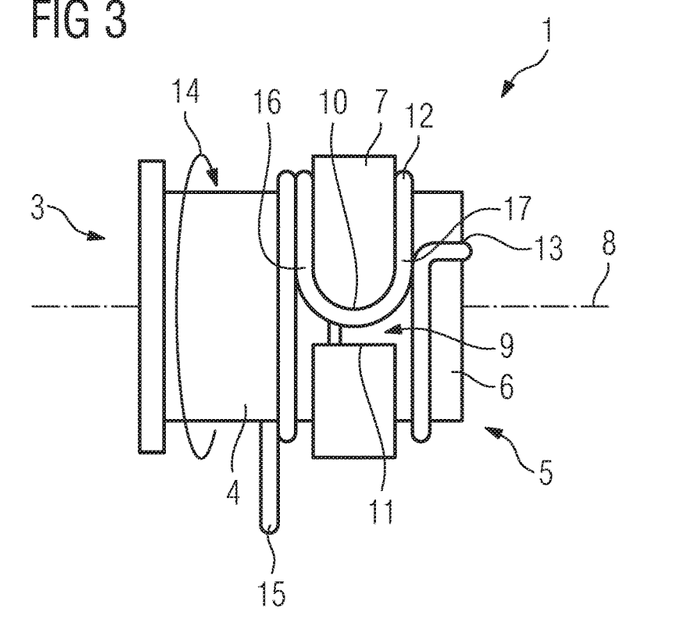
FIG. 3 shows the first assembly from FIG. 1 in a radial view in an unwinding state.

The winding-up operation or the unwinding operation will be explained below with reference to FIGS. 3 and 4. For this purpose, FIG. 3 shows the assembly 1 from FIG. 1 in the unwinding state. For this purpose, the first cylinder 3 has been rotated about the axis of rotation 8 of the guide device 2 in accordance with an arrow 14, and therefore the first cylinder 3 is rotated relative to the second cylinder 5. In the process, one end 15 of the first line 12, which end is unwound from the assembly 1, is extended. Of course, this illustration is purely schematic since the end 15 does not constitute the actual end of the first line 12. The actual end, on the contrary, lies in the region of the device to which the first line 12 is assigned, for example a detector or a radiation source. By means of the rotation of the first cylinder 3, the first line 12 is rotated with the first cylinder 3 in accordance with the arrow direction 14, and therefore the first line 12 moves the first guide element 7 at the same time. The first line 12 slides along the first deflecting side 10 or loops around the first guide element 7. As a result, the first line 12 is unwound in the region of the free end 15 from the first cylindrical surface 4 and is wound up onto the first cylindrical surface 4 in a region 16. The same length of the first line 12 is therefore always unwound from the first cylindrical surface 4, or wound up onto the latter, in the region 15 and is correspondingly wound up or unwound in the region 16. The position of the windings of the first line 12 on the first cylindrical surface 4 is displaced here along the axis of rotation 8 together with the first guide element 7 depending on the winding state. Consequently, the number of windings on the first cylindrical surface 4 remains substantially identical.

The first guide element 7, which moves relative to the second cylinder 5 likewise in the arrow direction 14, unwinds the first line 12 from the second cylindrical surface 6 in a region 17. The first line 12 loops here around the first deflecting side 10 and is therefore unwound from the second cylindrical surface 6 via the first deflecting side 10 onto the first cylindrical surface 4 and from there from the first cylindrical surface 4. In the unwinding movement illustrated in FIG. 3, the first guide element 7 moves away from the first cylinder 3 in the direction of the first deflection 13. Furthermore, the first guide element 7, as already described, moves in a rotatory manner about the axis of rotation 8 with the first line 12, which is moved with the first cylinder 3. The first guide element 7 is accordingly moved by the first line 12 in a forcibly coupled manner therewith because of the line looping therearound.

Figure 4:
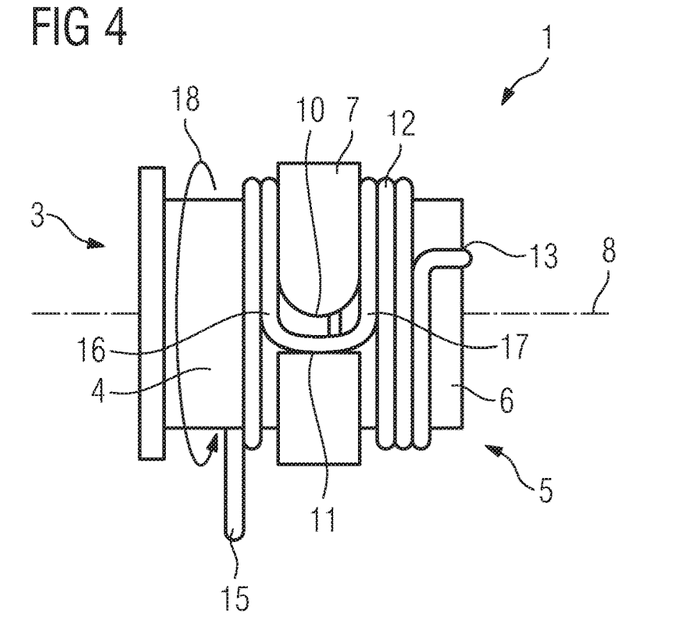
FIG. 4 shows the first assembly from FIG. 1 in a radial view in a winding-up state.

If the first cylinder 3 is moved in the opposed direction, by an arrow 18 in FIG. 4, the first assembly 1 passes into the winding-up state, or the first line 12 is wound up. The first line 12 is wound up here, from the free end 15, onto the first cylindrical surface 4 in accordance with the movement of the first cylinder 3 in the arrow direction 18. In the region 16, the first line 12 loops around the first guide element 7, and therefore the first line 12 lies against the second deflecting side 11. The first guide element 7 is accordingly rotated in the arrow direction 18 with the first cylinder 3 relative to the second cylinder 5. In the region 17, the first line 12, guided by the first guide element 7, is wound onto the second cylindrical surface 6 since the first guide element 7 rotates with the first cylinder 3 relative to the second cylindrical surface 6 about the axis of rotation 8 of the guide device 2. The first line 12 is wound up onto the second cylindrical surface 6, as a result of which the first guide element 7 is moved away from the first deflection 13 of the second cylinder 5 in the axial direction. Even during a transition from the unwinding state into the winding-up state or in general during winding up of the first line 12, the first guide element 7 consequently moves with the first cylinder 3 relative to the second cylinder 5 in a rotatory and translatory manner in the direction of the first cylinder 3.

The first line 12 is wound up here onto the first cylindrical surface 4 in the region 15 and is unwound from the first cylindrical surface 4 in the region 16. In the region 17 after passage through the deflection 9 of the first guide element 7, the first line 12 is wound up on the second cylindrical surface 6. As a result, the first line 12 is wound up in a plurality of windings on the second cylindrical surface 6, and therefore the entire first line 12 is first of all wound up onto the first cylindrical surface 4 and subsequently onto the second cylinder 5 by means of the first guide element 7.

Figure 5:
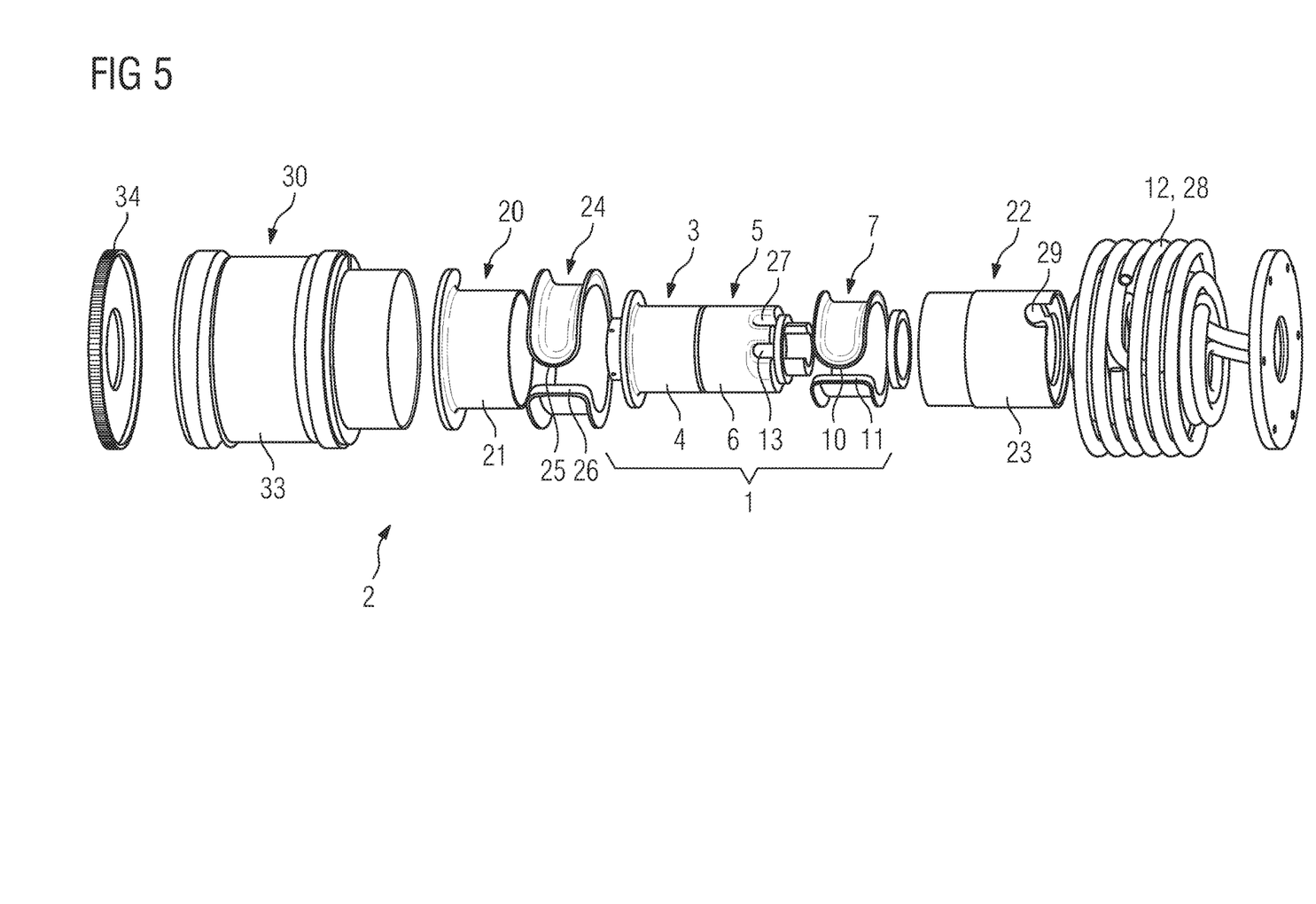
FIG. 5 is an exploded illustration of the guide device according to the invention.

FIG. 5 shows the guide device 2 in an exploded illustration. As can be seen, the first assembly 1 forms the radially inner assembly of the guide device 2, which has a second assembly 19 which is arranged coaxially with respect to the first assembly 1 and engages around the latter. The second assembly 19 has a third cylinder 20 with a third cylindrical surface 21, a fourth cylinder 22 with a fourth cylindrical surface 23, and a second guide element 24. The third cylinder 20 is rotatable here and the fourth cylinder 22 is static. The third cylinder 21 substantially corresponds to the first cylinder 3, and the fourth cylinder 22 corresponds to the second cylinder 5, which cylinders have already been described with respect to FIGS. 1 to 4. The second guide element 24 has a first deflecting side 25 and a second deflecting side 26. As can be seen, the second cylinder 5 has a second deflection 27 which is provided for a second line 28 which is assigned to the second assembly 19.

The second line 28 is guided out of the interior of the second cylinder 5 by the second deflection 27 of the second cylinder 5 and by a third deflection 29 in the fourth cylinder 22 and deflected onto the fourth cylinder surface 23. Subsequently, depending on the winding-up state or unwinding state, the second line 28 is directed analogously to the first line 12 in a corresponding manner via the second guide element 24 onto the third cylindrical surface 21 of the third cylinder 20.

FIG. 5 furthermore shows that the guide device 2 has a casing element 30 which is arranged coaxially with respect to the first assembly 1 and the second assembly 19 about the axis of rotation 8 of the guide device 2. The casing element 30 engages around the first assembly 1 and the second assembly 19. Accordingly, a nested coaxial construction of the first assembly 1, of the second assembly 19 and of the casing element 30 is produced. The nested construction is clarified in an axial view in FIG. 6. It should be noted here that a guide device with a further third line 31, which is discussed below, is shown according to FIG. 6. As can be seen, the first assembly 1 is arranged radially innermost. For the sake of clarity, only the first cylinder 3 and the second cylinder 5 are shown, with the first guide element 7 being hidden. Furthermore, the third cylinder 20 and the fourth cylinder 22 of the second assembly 19 are shown, wherein the second guide element 24 is likewise not illustrated. Consequently, the first assembly 1 is arranged radially within the second assembly 19. As can be seen, the first line 12 is guided on the first cylindrical surface 4 and the second cylindrical surface 6 within the third cylinder 20 and the fourth cylinder 22, respectively. The second line 28 runs between the third cylinder 20 or the fourth cylinder 22 and the casing element 30 on the third cylindrical surface 21 or the fourth cylindrical surface 23. This results in a nested construction which is particularly advantageous in respect of the required construction space. Furthermore, the first line 12 and the second line 28 can be wound up and unwound in an opposed direction depending on the winding direction or direction of movement of the rotatable cylinders 3, 20.

Figure 6:
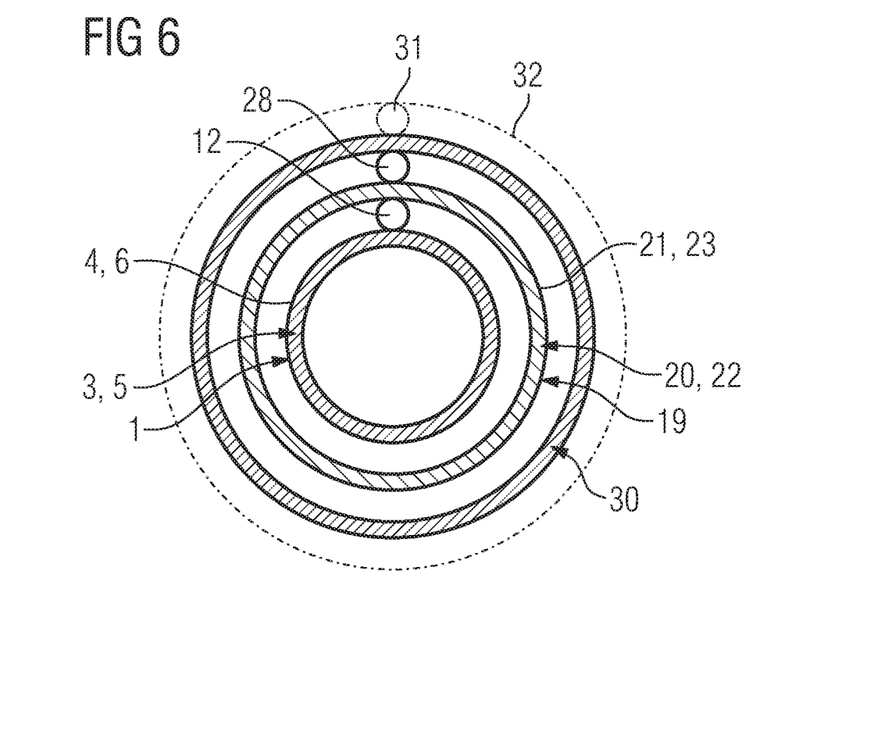
FIG. 6 shows a guide device according to the invention according to a second exemplary embodiment in the axial direction.

Furthermore, FIG. 6 shows that it is likewise possible to wind up or unwind any desired further number of lines in accordance with the principle of the invention. A third line 31 which runs between the casing element 30 and an element 32 shown by chain-dotted lines is therefore shown schematically by chain-dotted lines. If the guide device 2 is intended to be designed in such a manner that these three lines 12, 28, 31 are intended to be wound up or unwound separately from one another, the casing element 30 would have to be replaced by a third assembly which, in turn, has a rotatable fifth cylinder, a static sixth cylinder and a third guide element. The third assembly would accordingly take up the position of the casing element 30 in FIG. 6. The casing element 30 would accordingly take up the position of the element 32 in FIG. 6. The casing element 30 would again engage around all of the assemblies at the position of the element 32.

Figure 7:
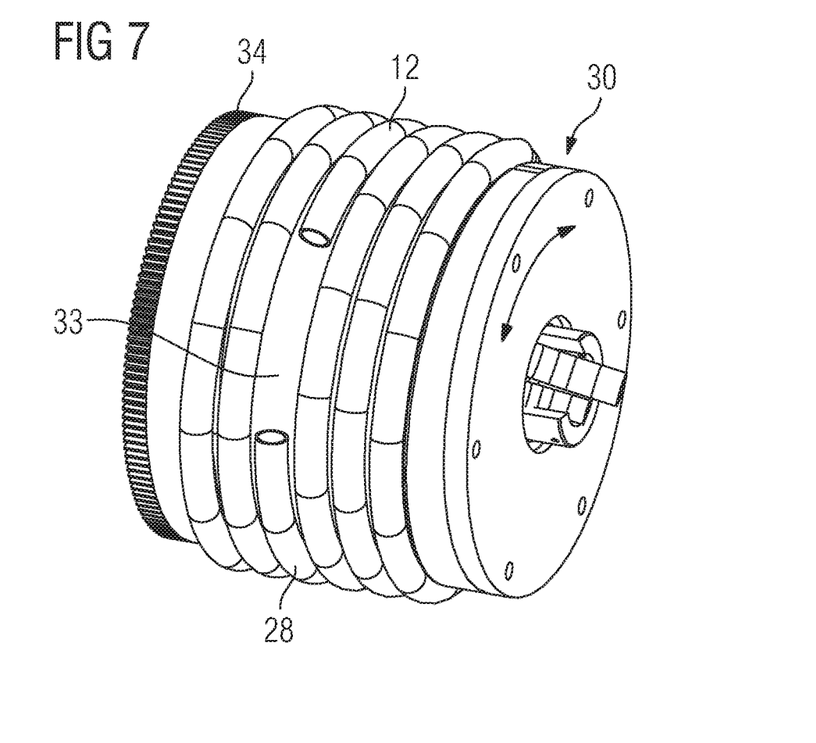
FIG. 7 is a perspective view of the guide device from FIG. 5.
Figure 8:
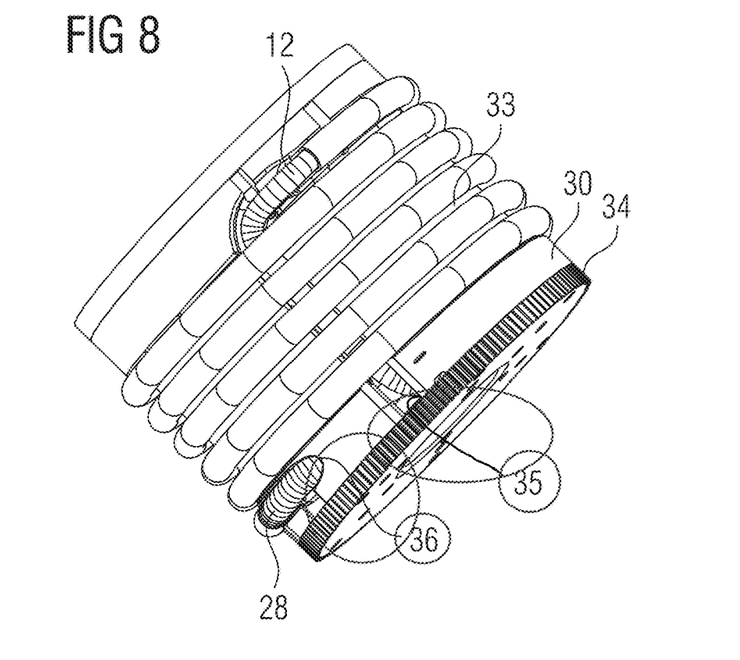
FIG. 8 is a perspective view of the guide device from FIG. 5.
Figure 9:
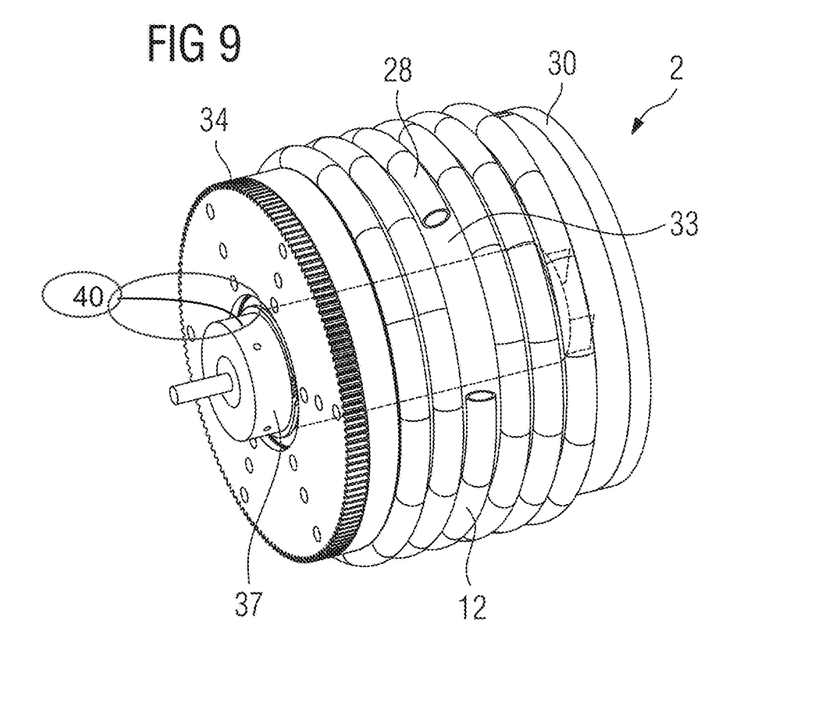
FIG. 9 is a perspective view of the guide device from FIG. 5 with a drive device.

FIGS. 7 to 9 show the guide device 2 with just two lines 12, 28. The winding of the lines 12, 28 on the casing element 30 will be described in more detail with reference to FIGS. 7 and 8. FIG. 7 shows that the lines 12, 28 have opposed winding directions on the outer surface 33 of the casing element 30. Consequently, during a rotation of the casing element 30 in the one direction, the first line 12 can be wound up and the second line 28 can be unwound, and vice versa. For this purpose, the casing element 30 has a coupling element 34 with which the casing element 30 can be coupled to a drive (not illustrated specifically). For example, the coupling element 34 is designed as a gear wheel. The first cylinder 3 and the third cylinder 20 are likewise coupled to the coupling element 34, and therefore a movement of the coupling element 34 is transmitted to the first cylinder 3, the third cylinder 20 and the casing element 30. It can optionally be taken into consideration here that the first assembly 1 guides the first line 12 onto a smaller circumference than the circumference of the second assembly 19. Accordingly, the length difference between the two lines 12, 28 that would arise when first and third cylinder 3, 10 rotate in the same direction has to be compensated for. This can be achieved, for example, via a line store or a gearing. The gearing has the effect that the circumferential travel of the first and third cylinder 3, 20 that is covered during a rotation is identical. As a result, it is ensured that the first line 12 is wound up or unwound in the same proportion as the second line 28, and vice versa.

FIG. 8 shows that the casing element 30 has a fourth deflection or deflection wall 35 and a fifth deflection or deflection wall 36 by means of which the corresponding lines 12, 28 are deflected from the interior of the casing element 30, i.e. from the first cylindrical surface 4 or the third cylindrical surface 21, onto the casing surface 33. The line 28 is wound up here from the direction of the coupling element 34 and the line 12 is wound up from the opposite end of the casing element 30, and therefore said lines lie opposite each other in the center of the casing element 30, as shown in FIG. 7.

FIG. 9 shows that the guide device 2 has a drive device 37 which is arranged in the interior of the first assembly 1. The drive device 37 is coupled to the coupling element 34 or to the casing element 30, the first cylinder 3 and the third cylinder 20. A defined movement of the casing element 30, of the first cylinder 3 and of the third cylinder 20 is therefore possible in such a manner that an unwinding of the first line 12 leads to a winding up of the second line 28, and vice versa. The drive device 37 can be coupled here to a C-arm (not illustrated specifically) or to any desired X-ray device to which the guide device 2 is assigned, and therefore a movement of the X-ray device leads to a uniform or identical movement of the drive device 37.

Figure 10:
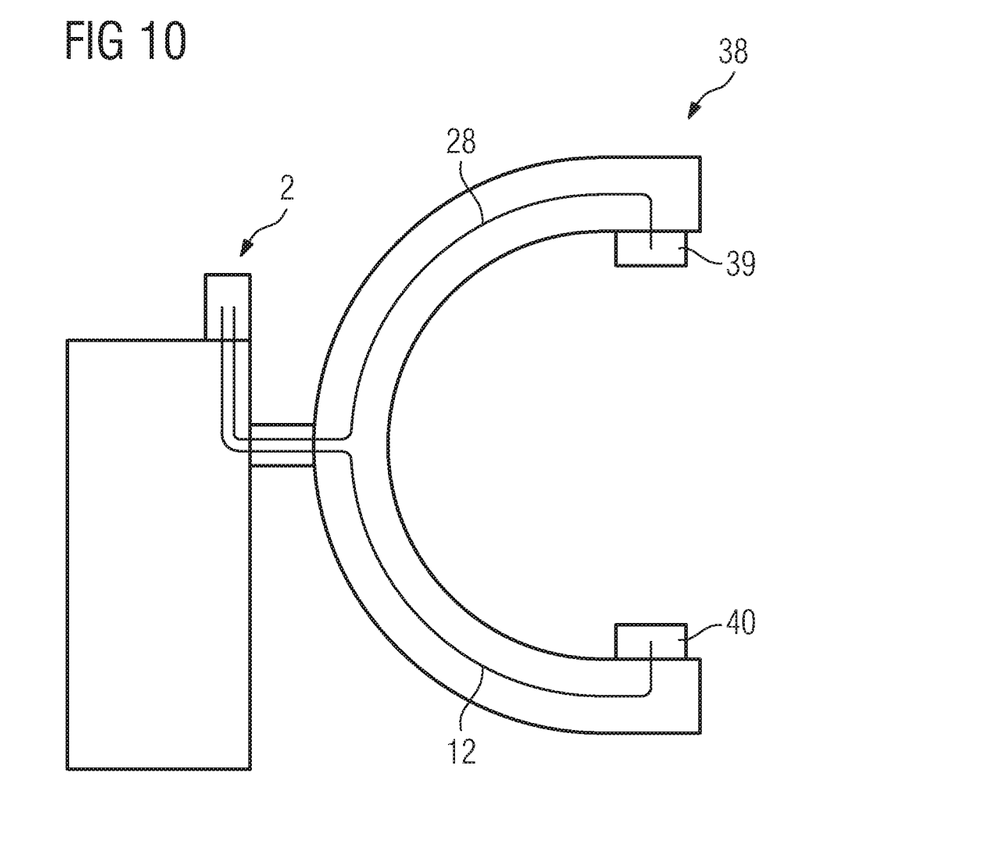
FIG. 10 shows a C-arm X-ray device according to the invention with a guide device according to the invention.

FIG. 10 shows an X-ray device 38 which is designed as a C-arm. The X-ray device 38 has an X-ray detector 39 and a radiation source 40. As can be seen, the X-ray device 38 furthermore has the guide device 2, wherein the two lines 12, 28 are guided to the X-ray detector 39 or the radiation source 40, in the housing of the X-ray device 38.

Although the invention has been illustrated and described more specifically in detail by the preferred exemplary embodiment, the invention is not restricted by the disclosed examples and other variations can be derived therefrom by a person skilled in the art without departing from the scope of protection of the invention.

The following is a summary list of reference numerals and the corresponding structure used in the above description of the invention:
1 Assembly
2 Guide device
3 First cylinder
4 First cylindrical surface
5 Second cylinder
6 Second cylindrical surface
7 First guide element
8 Axis of rotation
9 Deflecting portion
10 First deflecting side
11 Second deflecting side
12 First line
13 First deflection
14 Arrow direction
15 Free end
16 Region
17 Region
18 Arrow direction
19 Second assembly
20 Third cylinder
21 Third cylindrical surface
22 Fourth cylinder
23 Fourth cylindrical surface
24 Second guide element
25 First deflecting side
26 Second deflecting side
27 Second deflection
28 Second line
29 Third deflection
30 Casing element
31 Third line
32 Element
33 Outer surface
34 Coupling element
35 Fourth deflection
36 Fifth deflection
37 Drive device

The invention claimed is:

1. A guide device for at least one line, the guide device comprising:
a rotatable first cylinder having a first cylindrical surface;
a static second cylinder, adjoining said rotatable first cylinder in an axial direction and having a second cylindrical surface;
a first guide element configured for guiding the line on said first cylindrical surface and/or on said second cylindrical surface, said first guide element being arranged coaxially with respect to said rotatable first cylinder and said static second cylinder and being movable relative to said rotatable first cylinder and said static second cylinder; and
a rotatable third cylinder having a third cylindrical surface, a static fourth cylinder having a fourth cylindrical surface, and second guide element, each disposed about an axis of rotation and coaxially with said rotatable first cylinder and said static second cylinder;
wherein said third and fourth cylinders and said second guide element are configured to enable at least one further line to be wound up on, and to be unwound from, said third cylindrical surface of said third cylinder and/or said fourth cylindrical surface of said fourth cylinder;
wherein said rotatable first cylinder, said static second cylinder, and said first guide element are configured to enable the line to be wound up on said first cylindrical surface and/or said second cylindrical surface, or to be unwound therefrom, depending on a movement of said rotatable first cylinder; and
wherein said first guide element is rotatable about the axis of rotation and movable in the axial direction along the cylindrical surface of one or both of said rotatable first cylinder or static second cylinder.

2. The guide device according to claim 1, wherein a winding direction of the line to be wound up onto, or to be unwound from, said first and/or second cylindrical surfaces and a winding direction of said at least one further line differ from one another.

3. The guide device according to claim 1, wherein said first and second guide elements are rotatable about the axis of rotation and movable in the axial direction along the respective said cylindrical surface of said rotatable and/or static cylinder to which said first and second guide elements are assigned.

4. The guide device according to claim 1, wherein said static second cylinder is formed with a deflection wall for deflecting the line from an interior space of said static cylinder static second cylinder onto said second cylindrical surface.

5. The guide device according to claim 1, which comprises a casing element surrounding said static second cylinder and said rotatable cylinder and wherein said first guide element is disposed, at least in sections, coaxially and coupled to said rotatable first cylinder.

6. The guide device according to claim 1, wherein said guide element is U-shaped or C-shaped.

7. The guide device according to claim 1, wherein said guide device is coupled to a drive device that is configured to move said rotatable first cylinder.

8. An X-ray device, comprising a guide device according to claim 1.

9. The guide device according to claim 5, wherein said casing element has at least one deflection wall configured for deflecting the line from an interior of said casing element onto a casing surface of said casing element.

10. The guide device according to claim 5, wherein said casing element has deflection walls configured for deflecting two lines in an opposed winding direction onto a casing surface of said casing element.

11. The guide device according to claim 9, wherein said at least one deflection wall has a groove-shaped or trench-shaped portion on said casing surface.

12. The guide device according to claim 6, wherein a winding direction of the line, which is assigned to the first guide element, in a region of said rotatable first cylinder and in a region of said static second cylinder differ, and/or wherein the winding direction of the line is reversed at a deflecting portion.

13. The guide device according to claim 7, wherein said drive device is a hub motor disposed in an interior of said rotatable first cylinder or of a radially innermost said rotatable first cylinder.

14. The X-ray device according to claim 8, wherein said guide device is configured for guiding an electric line of a mobile C-arm.

15. The X-ray device according to claim 8, wherein a movement of said rotatable cylinder is coupled to a movement of the X-ray device.

16. The X-ray device according to claim 15, wherein the movement of said rotatable cylinder is coupled to a movement of a detector and an X-ray emitter about an orbital axis.

* * * * *